US011244059B2

(12) United States Patent
Yoon et al.

(10) Patent No.: US 11,244,059 B2
(45) Date of Patent: Feb. 8, 2022

(54) BLOCKCHAIN FOR MANAGING ACCESS TO MEDICAL DATA

(71) Applicant: International Business Machines Corporation, Armonk, NY (US)

(72) Inventors: Woong A. Yoon, Boxborough, MA (US); Alex Casella, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 232 days.

(21) Appl. No.: 15/982,626

(22) Filed: May 17, 2018

(65) Prior Publication Data

US 2019/0354693 A1 Nov. 21, 2019

(51) Int. Cl.
| | |
|---|---|
| *G06F 21/60* | (2013.01) |
| *G16H 10/60* | (2018.01) |
| *H04L 9/06* | (2006.01) |
| *H04L 9/14* | (2006.01) |
| *H04L 9/30* | (2006.01) |

(52) U.S. Cl.
CPC .......... *G06F 21/602* (2013.01); *G16H 10/60* (2018.01); *H04L 9/0637* (2013.01); *H04L 9/14* (2013.01); *H04L 9/30* (2013.01)

(58) Field of Classification Search
USPC ....................................................... 713/193
See application file for complete search history.

(56) References Cited

U.S. PATENT DOCUMENTS

| | | | | |
|---|---|---|---|---|
| 8,725,536 | B2* | 5/2014 | Deobhakta | G06Q 10/10 |
| | | | | 705/2 |
| 8,909,660 | B2* | 12/2014 | Campbell | G06Q 50/22 |
| | | | | 707/758 |
| 9,419,797 | B2 | 8/2016 | Scarisbrick et al. | |
| 9,646,168 | B2 | 5/2017 | Park et al. | |
| 9,665,734 | B2* | 5/2017 | Kaditz | G06F 21/6218 |
| 9,696,980 | B2* | 7/2017 | Dicks | G06F 8/654 |
| 9,760,681 | B2 | 9/2017 | Douglass | |
| 10,129,028 | B2* | 11/2018 | Kamakari | H04L 9/3073 |
| 10,305,869 | B2* | 5/2019 | Rosenberg | G16H 50/70 |
| 10,340,038 | B2* | 7/2019 | Witchey | G06F 21/00 |
| 10,701,054 | B2* | 6/2020 | Padmanabhan | H04L 63/101 |
| 10,719,501 | B1* | 7/2020 | Leise | G06F 16/182 |

(Continued)

OTHER PUBLICATIONS

Gupta et al.; "Adopting Blockchain Technology For Electronic Health Record Interoperability", Cognizant Technology Solutions, Aug. 8, 2017, pp. 1-10.

(Continued)

*Primary Examiner* — Amare F Tabor (57) ABSTRACT

An example operation may include one or more of receiving medical data of a user, creating metadata of the medical data which includes a unique identifier of the user and a searchable description of the medical data which describes one or more attributes included in the medical data but does not expose the medical data, encrypting the medical data to generate encrypted medical data, generating a data block having stored therein the created metadata of the medical data and the encrypted medical data, and storing the generated data block within a distributed ledger such that the generated data block is hash-linked to a previous data block on the distributed ledger.

20 Claims, 9 Drawing Sheets

(56) References Cited

U.S. PATENT DOCUMENTS

| | | |
|---|---|---|
| 2014/0324480 A1 | 10/2014 | Dufel et al. |
| 2015/0149208 A1* | 5/2015 | Lynch ................. G06F 21/6254 705/3 |
| 2015/0332283 A1 | 11/2015 | Witchey |
| 2016/0098522 A1 | 4/2016 | Weinstein |
| 2017/0039330 A1 | 2/2017 | Tanner et al. |
| 2017/0075941 A1 | 3/2017 | Finlow-Bates |
| 2017/0103163 A1 | 4/2017 | Emanuel et al. |
| 2017/0220815 A1 | 8/2017 | Ansari et al. |
| 2017/0293924 A1 | 10/2017 | Muzio |
| 2018/0082023 A1* | 3/2018 | Curbera .............. G06F 19/3418 |
| 2018/0167200 A1* | 6/2018 | High .................... A61B 5/1171 |
| 2019/0147137 A1* | 5/2019 | Gergely ............... H04L 9/3239 705/51 |
| 2019/0237169 A1* | 8/2019 | Culver ................. G06Q 20/387 |
| 2019/0348158 A1* | 11/2019 | Livesay ................ H04L 9/0891 |

OTHER PUBLICATIONS

Ivan, Drew; "Moving Toward a Blockchain-Based Method for the Secure Storage of Patient Records", National Institute of Standard Technology, Aug. 2, 2016, pp. 1-11.

Lundbaek et al.; "medixain: Robust Blockchain Optimization Enabling Individual Medical Wallet Architecture", University of Oxford, XAIN AG, Aug. 17, 2017, pp. 1-61.

Ratnayake, Yohan; "PKI Based Encryption For Document Sharing, Optimized Storage and Proof of Existence in the Cloud", KTH Royal Institute of Technology, 2015, pp. 1-31.

\* cited by examiner

FIG. 7

BLOCKCHAIN FOR MANAGING ACCESS TO MEDICAL DATA

TECHNICAL FIELD

This application generally relates to a system for managing access to sensitive medical information, and more particularly, to a blockchain for managing access to medical data.

BACKGROUND

A ledger is commonly defined as an account book of entry in which transactions are recorded and visible to authorized users. As another example, a distributed ledger is ledger that is replicated in whole or in part to multiple computing systems. One type of distributed ledger is a cryptographic distributed Ledger (CDL) which can have at least some of the following properties: irreversibility (once a transaction is recorded, it cannot be reversed), accessibility (any party can access the CDL in whole or in part), chronological and time-stamped (all parties know when a transaction was added to the ledger), consensus based (a transaction is added only if it is approved, typically unanimously, by parties on the network), verifiability (all transactions can be cryptographically verified). A blockchain is an example of a CDL. While the description and figures herein are described in terms of a blockchain, the instant application may apply equally to any type of cryptographic distributed ledger.

The Health Insurance Portability and Accountability Act (HIPAA) provides regulations which protect the privacy and security of health records. For example, the Security Rule of HIPAA establishes a national set of security standards for protecting certain health information that is held or transferred in electronic form. The Security Rule requires covered entities to maintain reasonable and appropriate administrative, technical, and physical safeguards for protecting electronic protected health information (e-PHI). Specifically, covered entities must ensure the confidentiality, integrity, and availability of all e-PHI they create, receive, maintain or transmit, identify and protect against reasonably anticipated threats to the security or integrity of the information, protect against reasonably anticipated, impermissible uses or disclosures, and ensure compliance by their workforce. Furthermore, the Security Rule's confidentiality requirements prohibit improper uses or disclosures to unauthorized persons. Organizations often undertake significant time and expense to ensure that information stored locally satisfies requirements for HIPAA, otherwise they face penalties from the regulations. As such, what is needed is a system which can facilitate the exchange of health-related information while alleviating the burden on organizations involved in the exchange.

SUMMARY

One example embodiment may provide a method that includes one or more of receiving medical data of a user, creating metadata of the medical data which includes a unique identifier of the user and a searchable description of the medical data which describes one or more attributes included in the medical data but does not expose the medical data, encrypting the medical data to generate encrypted medical data, generating a data block having stored therein the created metadata of the medical data and the encrypted medical data, and storing the generated data block within a distributed ledger such that the generated data block is hash-linked to a previous data block on the distributed ledger.

Another example embodiment may provide a system that includes one or more network interface configured to receive medical data of a user, and a processor configured to perform one or more of create metadata of the medical data which includes a unique identifier of the user and a searchable description of the medical data which describes one or more attributes included in the medical data but does not expose the medical data, encrypt the medical data to generate encrypted medical data, generate a data block that has stored therein the created metadata of the medical data and the encrypted medical data, and store the generated data block within a distributed ledger such that the generated data block is hash-linked to a previous data block on the distributed ledger.

A further example embodiment may provide a non-transitory computer readable medium comprising instructions, that when read by a processor, cause the processor to perform one or more of receiving medical data of a user, creating metadata of the medical data which includes a unique identifier of the user and a searchable description of the medical data which describes one or more attributes included in the medical data but does not expose the medical data, encrypting the medical data to generate encrypted medical data, generating a data block having stored therein the created metadata of the medical data and the encrypted medical data, and storing the generated data block within a distributed ledger such that the generated data block is hash-linked to a previous data block on the distributed ledger.

DETAILED DESCRIPTION

It will be readily understood that the instant components, as generally described and illustrated in the figures herein, may be arranged and designed in a wide variety of different configurations. Thus, the following detailed description of the embodiments of at least one of a method, apparatus, non-transitory computer readable medium and system, as represented in the attached figures, is not intended to limit the scope of the application as claimed, but is merely representative of selected embodiments.

The instant features, structures, or characteristics as described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" may have been used in the description of embodiments, the application may be applied to many types of network data, such as, packet, frame, datagram, etc. The term "message" also includes packet, frame, datagram, and any equivalents thereof. Furthermore, while certain types of messages and signaling may be depicted in exemplary embodiments they are not limited to a certain type of message, and the application is not limited to a certain type of signaling.

The example embodiments are directed to methods, devices, networks and/or systems, which support a blockchain system that provides for secure consent and exchange of health information while satisfying privacy and security regulations. The use of a blockchain provides numerous benefits because it solves the need for trust and security of health information by providing an immutable ledger where users (e.g., patients, etc.) can view consent and data access history of their health information provided to consumers (e.g., medical providers, insurers, etc.). The blockchain system provides a secure and efficient way to store patient data and control access to patient data based on patient consent. Furthermore, the blockchain provides an audit trail that makes health data exchange more easily regulated.

Blockchain is different from a traditional database in that blockchain is not a central storage but rather a decentralized, immutable, and secure storage, where nodes must share in changes to records in the storage. Some properties that are inherent in blockchain and which help implement the blockchain include, but are not limited to, an immutable ledger, smart contracts, security, privacy, decentralization, consensus, endorsement, accessibility, and the like, which are further described herein. According to various aspects, the trust and security of health information is implemented due to the immutable ledger, decentralization, consensus, endorsement, hidden data, restrictions on access, and smart contracts, which are inherent and unique to blockchain.

For example, the blockchain system relies on an immutable ledger to store patient health records. The blockchain leverages smart contract logic to store and view patient data, control access, and view medical history information. The system makes it much more secure to store and transfer sensitive patient health data, thus providing an improvement to the security and privacy aspects of traditional methods. Data is stored on a distributed ledger system where each node has a copy of the data. To allow a transaction to be committed to the ledger, there must be consensus between the nodes and follow the endorsement policy. The system greatly improves accessibility for patients and healthcare providers to provide consent, transfer data, access data, and keep a record. Furthermore, the health data is not completely hidden from data consumers but is partially revealed through metadata. The metadata may be created by the smart contract and stored on the blockchain. The metadata may include a description of the underlying health information (e.g., type of records, doctor's name, date, etc.) without disclosing protected sensitive health information.

The example embodiments provide numerous benefits over a traditional database. For example, through the blockchain the embodiments provide for trusted and accountable storage via an immutable ledger that can only be modified based on consensus of nodes in the blockchain. Meanwhile, a traditional database could not be used to implement the example embodiments because a traditional database does not provide the same level of trust and accountability of data. That is, a traditional database is subject to a single entity that controls access to information whereas the blockchain system herein provides for distributed access which must only be provided when a consensus among the nodes is achieved. Furthermore, the distributed ledger of the blockchain maintains an agreed upon audit trial that provides a layer of accountability not possible in the single-entity controlled database. Furthermore, the metadata information is created and made available through the blockchain thereby enabling a search of the medical data to be performed without divulging the underlying confidential information.

A blockchain is a distributed system which includes multiple nodes that communicate with each other. A blockchain operates programs called chaincode (e.g., smart contracts, etc.), holds state and ledger data, and executes transactions. Some transactions are operations invoked on the chaincode. In general, blockchain transactions typically must be "endorsed" by certain blockchain members and only endorsed transactions may be committed to the blockchain and have an effect on the state of the blockchain. Other transactions which are not endorsed are disregarded. There may exist one or more special chaincodes for management functions and parameters, collectively called system chaincodes.

Nodes are the communication entities of the blockchain system. A "node" may perform a logical function in the sense that multiple nodes of different types can run on the same physical server. Nodes are grouped in trust domains and are associated with logical entities that control them in various ways. Nodes may include different types, such as a client or submitting-client node which submits a transaction-invocation to an endorser (e.g., peer node), and broadcasts transaction-proposals to an ordering service (e.g., ordering node). Another type of node is a peer node which can receive client submitted transactions, commit the transactions and maintain a state and a copy of the ledger of blockchain transactions. Peers can also have the role of an endorser, although it is not a requirement. An ordering-service-node or orderer is a node running the communication service for all nodes, and which implements a delivery guarantee, such as a broadcast to each of the peer nodes in the system when committing transactions and modifying a world state of the blockchain, which is another name for the initial blockchain transaction which normally includes control and setup information.

A distributed ledger is a sequenced, tamper-resistant record of all state transitions of a blockchain. State transitions may result from chaincode invocations (i.e., transactions) submitted by participating parties (e.g., client nodes, ordering nodes, endorser nodes, peer nodes, etc.). A transaction may result in a set of asset key-value pairs being committed to the ledger as one or more operands, such as creates, updates, deletes, and the like. The ledger includes a blockchain (also referred to as a chain) which is used to store an immutable, sequenced record in blocks. The ledger also includes a state database which maintains a current state of the blockchain. There is typically one ledger per channel. Each peer node maintains a copy of the ledger for each channel of which they are a member.

A chain is a transaction log which is structured as hash-linked blocks, and each block contains a sequence of N transactions where N is equal to or greater than one. The block header includes a hash of the block's transactions, as well as a hash of the prior block's header. In this way, all transactions on the ledger may be sequenced and cryptographically linked together. Accordingly, it is not possible to tamper with the ledger data without breaking the hash links. A hash of a most recently added blockchain block represents every transaction on the chain that has come before it, making it possible to ensure that all peer nodes are in a consistent and trusted state. The chain may be stored on a peer node file system (i.e., local, attached storage, cloud, etc.), efficiently supporting the append-only nature of the blockchain workload.

The current state of the immutable ledger represents the latest values for all keys (or key/value pairs) that are included in the chain transaction log. Because the current state represents the latest key values known to a channel, it is sometimes referred to as a world state. Chaincode invocations execute transactions against the current state data of the distributed ledger. To make these chaincode interactions efficient, the latest values of the keys may be stored in a state database. The state database may be simply an indexed view into the chain's transaction log, it can therefore be regenerated from the chain at any time. The state database may automatically be recovered (or generated if needed) upon peer node startup, and before transactions are accepted.

Figure 1:
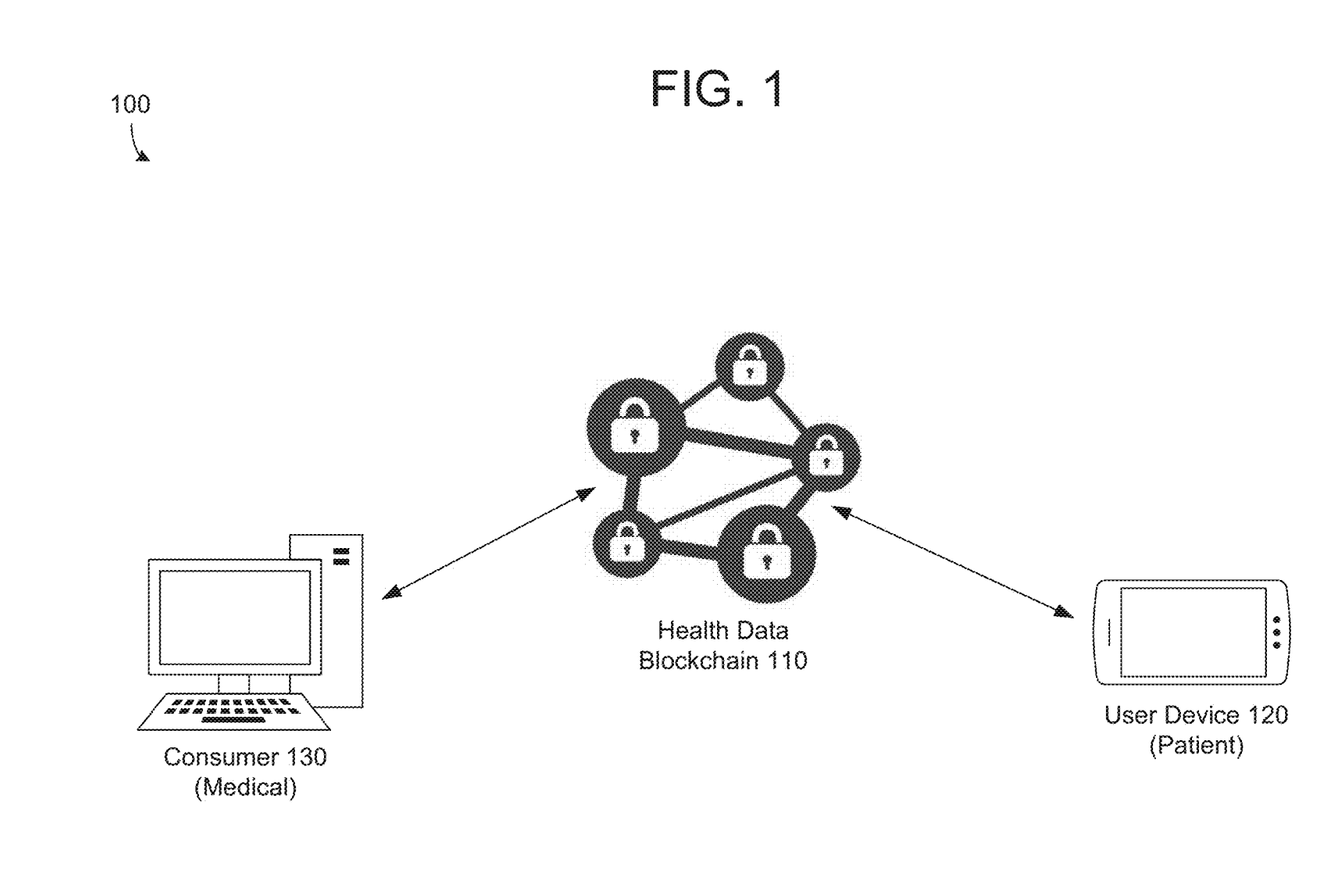
FIG. 1 is a diagram illustrating a blockchain network for providing secure consent and access to medical data, according to example embodiments.

FIG. 1 illustrates a blockchain network 100 for providing secure consent and access to medical data, according to example embodiments. Referring to FIG. 1, the blockchain network 100 includes a user device 120 which is capable of submitting health information to a health data blockchain 110. Furthermore, the blockchain network 100 includes a consumer device 130 capable of requesting medical data of the user stored on the blockchain 110. The blockchain 110 may be composed of a plurality of nodes which include a plurality of peer nodes. Each peer node of the health data blockchain 110 may interact with and receive requests from the user device 120 and/or the consumer device 130 for accessing the health data blockchain 110.

When the user device 120 submits medical data to the health data blockchain 110 for storage therein, the individual nodes of the health data blockchain 110 must reach a consensus on the storage of the medical data based on one or more predetermined policies which may be implemented by a smart contract. Furthermore, the medical data may be stored as a block (or more than one block) on a distributed ledger which is replicated across the nodes in the health data blockchain 110.

The consumer device 130 may access a peer node of the health data blockchain 110 and perform a search of medical data stored therein. However, rather than search the actual data, the search results may only include metadata of the medical data. The metadata may not expose the underlying medical data but instead may be a generic description, a date/time, and doctor's name, and the like. Through the search, the consumer device 130 may request for a particular user's medical data (e.g., user of user device 120, etc.) and receive access to the medical data only when consent is received by the health data blockchain 110 from the user device 120. For example, the consent may be received via a message and may trigger the health data blockchain 110 to unlock a key which was used to encrypt the medical data. Furthermore, the key may be encrypted using a public key of the consumer 130 and provided to the consumer 130 for use in decrypting the medical data of the user.

Figure 2A:
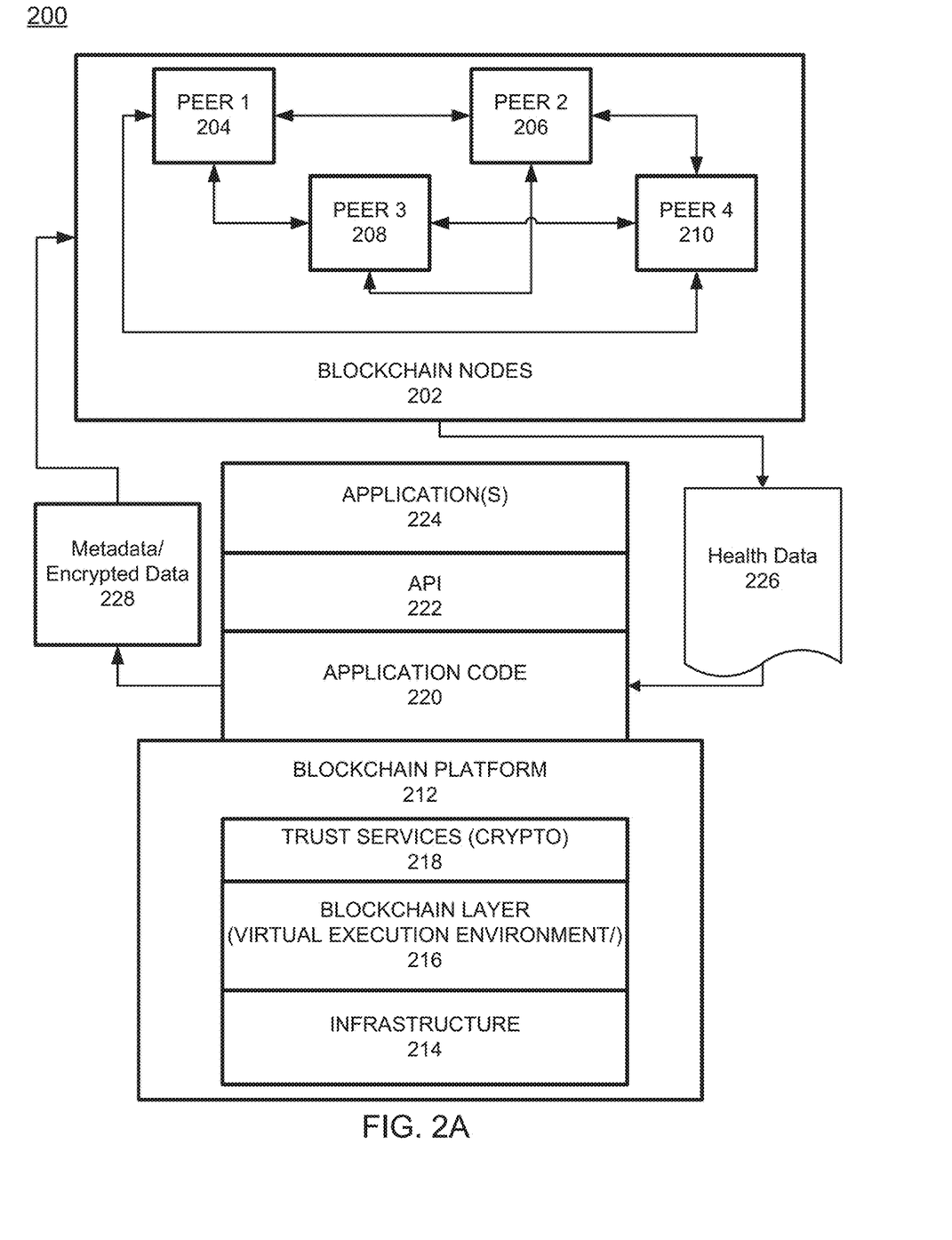
FIG. 2A is a diagram illustrating a peer node blockchain architecture configuration, according to example embodiments.

FIG. 2A illustrates a blockchain architecture configuration 200, according to example embodiments. As an example, the blockchain architecture configuration 200 may represent the health data blockchain 110 shown in FIG. 1. Referring to FIG. 2A, the blockchain architecture 200 may include certain blockchain elements, for example, a group of blockchain nodes 202. The blockchain nodes 202 may include one or more nodes 204-210. (4 nodes are depicted by example only). These nodes participate in a number of activities, such as blockchain transaction addition and validation process (consensus). One or more of the blockchain nodes 204-210 may endorse transactions and may provide an ordering service for all blockchain nodes in the architecture 200. A blockchain node may initiate a blockchain authentication and seek to write to a blockchain immutable ledger stored in blockchain layer 216, a copy of which may also be stored on the underpinning physical infrastructure 214. The blockchain configuration may include one or applications 224 which are linked to application programming interfaces (APIs) 222 to access and execute stored program/application code 220 (e.g., chaincode, smart contracts, etc.) which can be created according to a customized configuration sought by participants and can maintain their own state, control their own assets, and receive external information. This can be deployed as a transaction and installed, via appending to the distributed ledger, on all blockchain nodes 204-210.

The blockchain base or platform 212 may include various layers of blockchain data, services (e.g., cryptographic trust services, virtual execution environment, etc.), and underpinning physical computer infrastructure that may be used to receive and store new transactions and provide access to auditors which are seeking to access data entries. The blockchain layer 216 may expose an interface that provides access to the virtual execution environment necessary to process the program code and engage the physical infrastructure 214. Cryptographic trust services 218 may be used to verify transactions such as asset exchange transactions and keep information private.

The blockchain architecture configuration of FIG. 2A may process and execute program/application code 220 via one or more interfaces exposed, and services provided, by blockchain platform 212. The code 220 may control blockchain assets. For example, the code 220 can store and transfer data, and may be executed by nodes 204-210 in the form of a smart contract and associated chaincode with conditions or other code elements subject to its execution. As a non-limiting example, smart contracts may be created to execute reminders, updates, and/or other notifications subject to the changes, updates, etc. The smart contracts can themselves be used to identify rules associated with authorization and access requirements of health data and consent/usage of the ledger. For example, health-related information 226 may be processed by one or more processing entities (e.g., virtual machines) included in the blockchain layer 216. The health-related information 226 may be encrypted via a symmetric key. Furthermore, a result 228 of the encryption may be stored on the blockchain layer 216 and may include the encrypted health information, the metadata, the symmetric key (encrypted with a public key), and the like. The physical infrastructure 214 may be utilized to retrieve any of the data or information described herein.

Within chaincode, a smart contract may be created via a high-level application and programming language, and then written to a block in the blockchain. The smart contract may include executable code which is registered, stored, and/or replicated with a blockchain (e.g., distributed network of blockchain peers). A transaction is an execution of the smart contract code which can be performed in response to conditions associated with the smart contract being satisfied. The executing of the smart contract may trigger a trusted modification(s) to a state of a digital blockchain ledger. The modification(s) to the blockchain ledger caused by the smart contract execution may be automatically replicated throughout the distributed network of blockchain peers through one or more consensus protocols.

The smart contract may write data to the blockchain in the format of key-value pairs. Furthermore, the smart contract code can read the values stored in a blockchain and use them in application operations. The smart contract code can write the output of various logic operations into the blockchain. The code may be used to create a temporary data structure in a virtual machine or other computing platform. Data written to the blockchain can be public and/or can be encrypted and maintained as private. The temporary data that is used/generated by the smart contract is held in memory by the supplied execution environment, then deleted once the data needed for the blockchain is identified.

A chaincode may include the code interpretation of a smart contract, with additional features. As described herein, the chaincode may be program code deployed on a computing network, where it is executed and validated by chain validators together during a consensus process. The chaincode receives a hash and retrieves from the blockchain a hash associated with the data template created by use of a previously stored feature extractor. If the hashes of the hash identifier and the hash created from the stored identifier template data match, then the chaincode sends an authorization key to the requested service. The chaincode may write to the blockchain data associated with the cryptographic details. In FIG. 2A, the health-related information 226 may be used to generate metadata of the health information 226 which describes the health information and the user, but which does not reveal the health information. Furthermore, the health related information 226 may be encrypted to generate a result 228 which also includes the metadata, and the result 228 including the encrypted health information and the unencrypted metadata may be provided to one or more of the nodes 204-210.

Figure 2B:
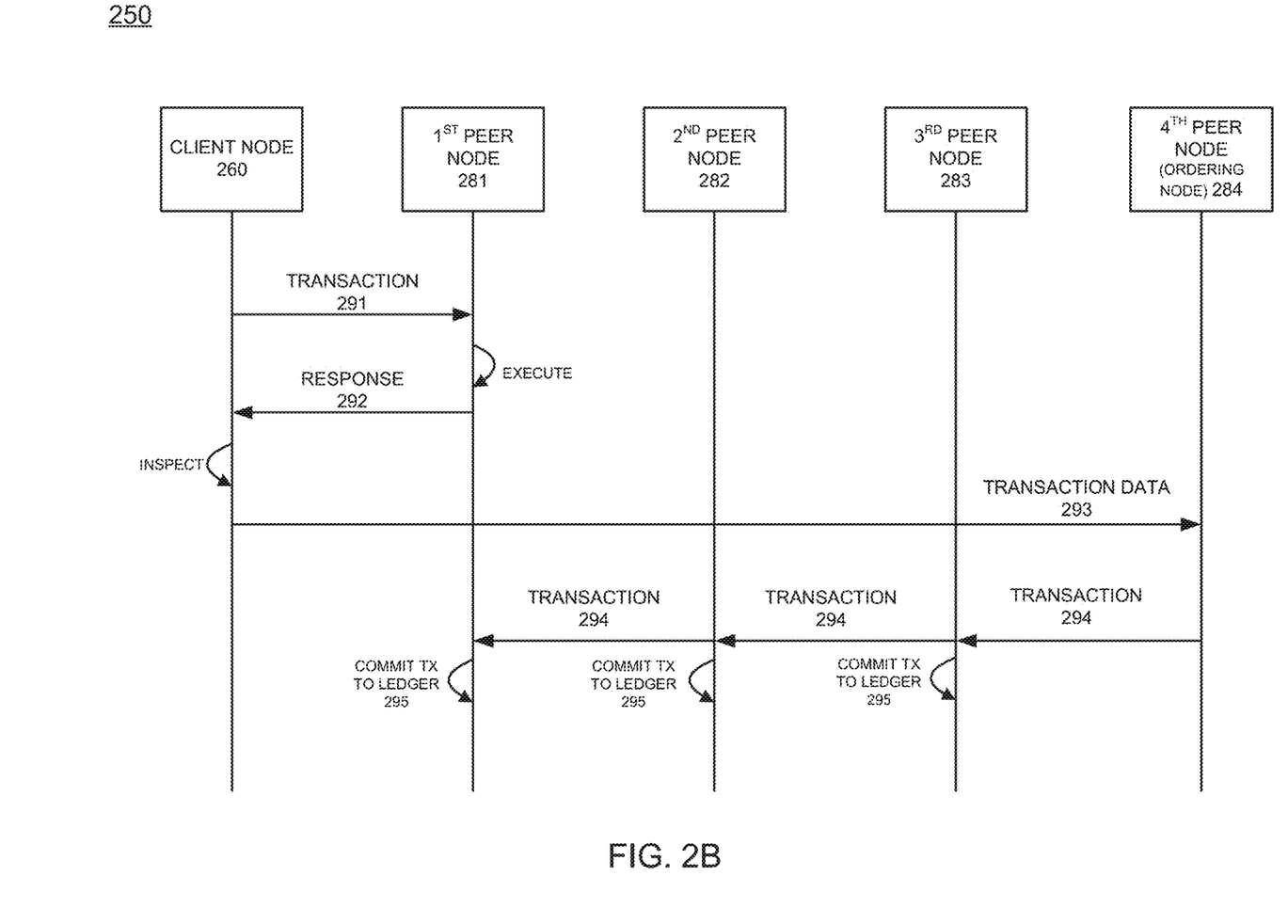
FIG. 2B is a diagram illustrating a peer node communication process, according to example embodiments.

FIG. 2B illustrates an example of a transactional flow 250 between nodes of the blockchain in accordance with an example embodiment. Referring to FIG. 2B, the transaction flow may include a transaction proposal 291 sent by an application client node 260 to an endorsing peer node 281. For example, the transaction proposal may include a request to store health-related data. The endorsing peer 281 may verify the client signature and execute a chaincode function to initiate the transaction. The output may include the chaincode results, a set of key/value versions that were read in the chaincode (read set), and the set of keys/values that were written in chaincode (write set). The proposal response 292 is sent back to the client 260 along with an endorsement signature, if approved. The client 260 assembles the endorsements into a transaction payload 293 and broadcasts it to an ordering service node 284. The ordering service node 284 then delivers ordered transactions as blocks to all peers 281-283 on a channel. Before committal to the blockchain, each peer 281-283 may validate the transaction. For example, the peers may check the endorsement policy to ensure that the correct allotment of the specified peers have signed the results and authenticated the signatures against the transaction payload 293.

Referring again to FIG. 2B, the client node 260 initiates the transaction 291 by constructing and sending a request to the peer node 281, which is an endorser. The client 260 may include an application leveraging a supported software development kit (SDK), such as NODE, JAVA, PYTHON, and the like, which utilizes an available API to generate a transaction proposal. The proposal is a request to invoke a chaincode function so that data can be read and/or written to the ledger (i.e., write new key value pairs for health data assets). The SDK may serve as a shim to package the transaction proposal into a properly architected format (e.g., protocol buffer over a remote procedure call (RPC)) and take the client's cryptographic credentials to produce a unique signature for the transaction proposal.

In response, the endorsing peer node 281 may verify (a) that the transaction proposal is well formed, (b) the transaction has not been submitted already in the past (replay-attack protection), (c) the signature is valid, and (d) that the submitter (client 260, in the example) is properly authorized to perform the proposed operation on that channel. The endorsing peer node 281 may take the transaction proposal inputs as arguments to the invoked chaincode function. The chaincode is then executed against a current state database to produce transaction results including a response value, read set, and write set. However, no updates are made to the ledger at this point. In 292, the set of values, along with the endorsing peer node's 281 signature is passed back as a proposal response 292 to the SDK of the client 260 which parses the payload for the application to consume.

In response, the application of the client 260 inspects/verifies the endorsing peers signatures and compares the proposal responses to determine if the proposal response is the same. If the chaincode only queried the ledger, the application would inspect the query response and would typically not submit the transaction to the ordering node service 284. If the client application intends to submit the transaction to the ordering node service 284 to update the ledger, the application determines if the specified endorsement policy has been fulfilled before submitting (i.e., did all peer nodes necessary for the transaction endorse the transaction). Here, the client may include only one of multiple parties to the transaction. In this case, each client may have their own endorsing node, and each endorsing node will need to endorse the transaction. The architecture is such that even if an application selects not to inspect responses or otherwise forwards an unendorsed transaction, the endorsement policy will still be enforced by peers and upheld at the commit validation phase.

After successful inspection, in step 293 the client 260 assembles endorsements into a transaction and broadcasts the transaction proposal and response within a transaction message to the ordering node 284. The transaction may contain the read/write sets, the endorsing peers signatures and a channel ID. The ordering node 284 does not need to inspect the entire content of a transaction in order to perform its operation, instead the ordering node 284 may simply receive transactions from all channels in the network, order them chronologically by channel, and create blocks of transactions per channel.

The blocks of the transaction are delivered from the ordering node 284 to all peer nodes 281-283 on the channel. The transactions 294 within the block are validated to ensure any endorsement policy is fulfilled and to ensure that there have been no changes to ledger state for read set variables since the read set was generated by the transaction execution. Transactions in the block are tagged as being valid or invalid. Furthermore, in step 295 each peer node 281-283 appends the block to the channel's chain, and for each valid transaction the write sets are committed to current state database. An event is emitted, to notify the client application that the transaction (invocation) has been immutably appended to the chain, as well as to notify whether the transaction was validated or invalidated.

Figure 3:
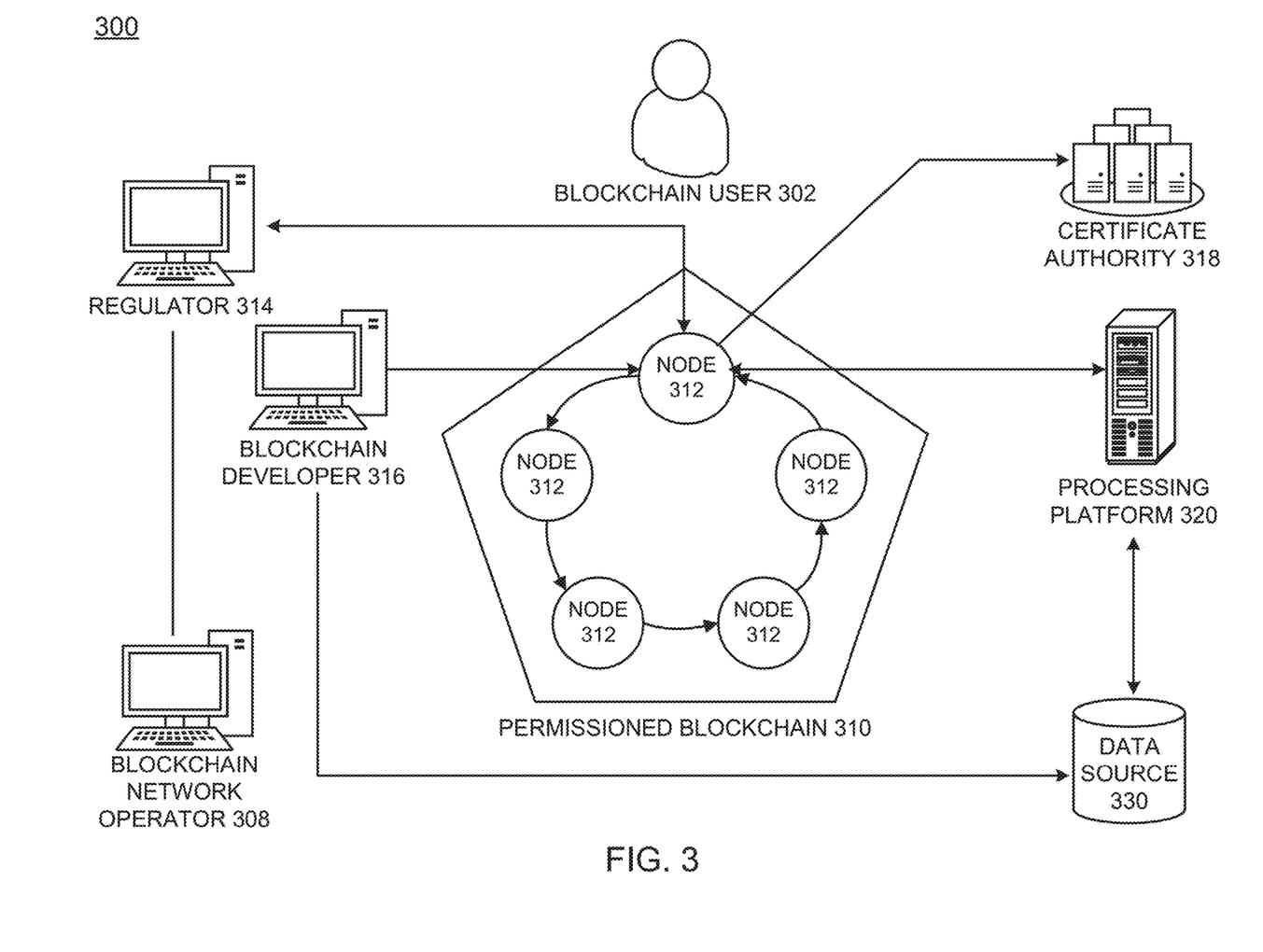
FIG. 3 is a diagram illustrating a permissioned blockchain network, according to example embodiments.

FIG. 3 illustrates an example of a permissioned blockchain network 300, which features a distributed, decentralized peer-to-peer architecture, and a certificate authority 318 managing user roles and permissions. In this example, the blockchain user 302 may submit a transaction to the permissioned blockchain network 310. In this example, the transaction can be a deploy, invoke or query, and may be issued through a client-side application leveraging an SDK, directly through a REST API, or the like. Trusted business networks may provide access to regulator systems 314, such as auditors (the Securities and Exchange Commission in a U.S. equities market, for example). Meanwhile, a blockchain network operator system of nodes 308 manage member permissions, such as enrolling the regulator system 310 as an "auditor" and the blockchain user 302 as a "client." An auditor could be restricted only to querying the ledger whereas a client could be authorized to deploy, invoke, and query certain types of chaincode and store and consume health-related data.

A blockchain developer system 316 writes chaincode and client-side applications. The blockchain developer system 316 can deploy chaincode directly to the network through a REST interface. To include credentials from a traditional data source 330 in chaincode, the developer system 316 could use an out-of-band connection to access the data. In this example, the blockchain user 302 connects to the network through a peer node 312. Before proceeding with any transactions, the peer node 312 retrieves the user's enrollment and transaction certificates from the certificate authority 318. In some cases, blockchain users must possess these digital certificates in order to transact on the permissioned blockchain network 310. Meanwhile, a user attempting to drive chaincode may be required to verify their credentials on the traditional data source 330. To confirm the user's authorization, chaincode can use an out-of-band connection to this data through a traditional processing platform 320.

Normally, it is difficult to implement a medical data exchange system because of strong regulations regarding patient consent and medical data exchange monitoring and auditing. The example embodiments provide a solution to this problem and implement a more efficient way to share patient medical data securely according to patient consent with the system and method described herein using blockchain, because blockchain provides an immutable history of record of data transactions as well as controlled storage and access of medical data in a distributed manner such that one single entity is not in control of the storage.

Figure 4:
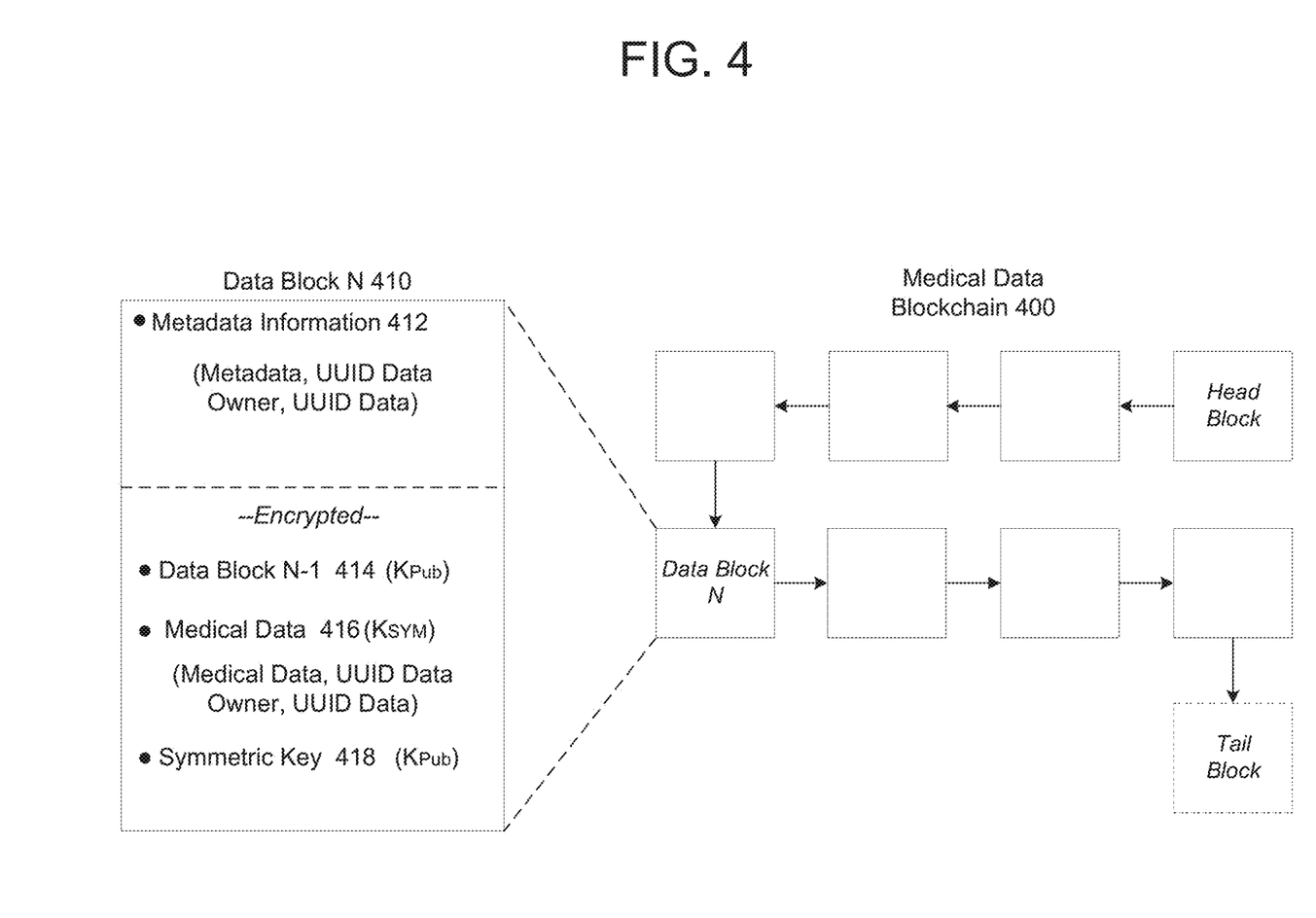
FIG. 4 is a diagram illustrating a distributed ledger including a plurality of linked data blocks storing medical data, according to example embodiments.

FIG. 4 illustrates a distributed ledger (i.e., blockchain) 400 including a plurality of linked data blocks storing medical data, according to example embodiments. FIG. 4 also illustrates an example of contents which may be included in a data block 410 of the blockchain 400. In this example, the chain includes a single chain with one head and one tail that may continue to grow as new records/blocks are stored. However, this design is merely for convenience of description and it should be appreciated that the blockchain may have multiple tails, multiple heads, etc., with different branches moving off of various chains.

The blockchain system and method described herein manages consent using encryption and decryption keys. Each user (data owner or data consumer) of the system has their own public key (Kpb), private key (Kpv), and unique user ID (UUID). The public keys may be disclosed to other parties within the blockchain network via a key management service (KMS). An example of data owner and consumer is patient and healthcare provider respectively. This system and method contains 4 steps. Each step may be stored on the blockchain ledger 400 for record keeping and provenance.

In a first step, a data owner uploads medical data to the blockchain 400. For example, the medical data may include treatment information, medical records, medication information, doctor's notes, patient notes, other medical information, and the like. In this step, the data owner (or blockchain node acting on behalf of the data owner) generates a UUID of the data, a symmetric key for the data, and metadata of the medical data. The metadata may not expose the medical data but may provide a searchable description of the medical data. To generate the data block 410, the data owner may store the metadata 412 information within the block 410. The metadata information may include the metadata, the UUID of the data, and a UUID of the data owner (which may be provided to the data owner or generated by the data owner.

Furthermore, the data owner encrypts the medical data with the symmetric key to generate encrypted medical data 416. The data owner may also encrypt the symmetric key with a public key of the data owner to generate an encrypted key 418. Here, the encrypted medical data 416 and the encrypted key 418 may be stored in the data block 410. Also stored in the data block 410 may be a hash of data of a previous block 418 which is encrypted using the public key of the data owner (or another key known to other nodes). The hash of data of the previous block 418 may include medical data that is stored in the previous block, metadata, UUID of the data, UUID of the data owner, and the like. By including a hash of the data from the previous block 418 in the data block 410, a hash-link may be created between the two blocks.

In a second step, a data consumer may search for and request access to the medical data stored in the first step. For example, a blockchain node may output a search interface (e.g., user interface, search bar, etc.) that enables the data consumer to search through metadata of medical records stored on the medical data blockchain 400 without divulging the underlying medical data. When the consumer finds a UUID of data/data owner they are interested in, the data consumer may retrieve a public key of the data owner (e.g., via a KMS) using the UUID of the data owner. Furthermore, the consumer may generate a data block and store a data block on the medical data blockchain 400 thereby requesting the medical data of the data owner. For example, the data consumer may generate a data block including a UUID of the data consumer (signed by the data consumer), and a UUID of data they are interested in (revealed during the metadata search). Here, the elements of the data block may be encrypted using the public key of the data owner. Furthermore, the data consumer may send the request by saving the encrypted block to the medical data blockchain 400.

The data owner may detect the request from the data consumer via the medical data blockchain 400. Here, the data owner may receive the request including the UUID of the data owner and the UUID of the data consumer. The data owner may decrypt the UUID of the data being requested based on the data owner's private key. The data owner may also verify the signature of the data consumer. When the data owner determines to provide consent, in step 3, the data owner may retrieve the encrypted symmetric key from the medical data blockchain 400, decrypt the encrypted symmetric key with the private key of the data owner, encrypt the decrypted symmetric key but now with a public key of the data consumer, and store the encrypted symmetric key on the medical data blockchain 400 along with consent. The consent may include the UUID of the data owner, the UUID of the data consumer, and the UUID of the data.

In step four, the data consumer may acquire the consent from the medical data blockchain 400, acquire the symmetric key by decrypting the symmetric key using the private key of the data consumer, and decrypt the requested data from the blockchain using the acquired symmetric key. Accordingly, both the storage and consent of the medical data may be performed via the blockchain 400.

Figure 5:
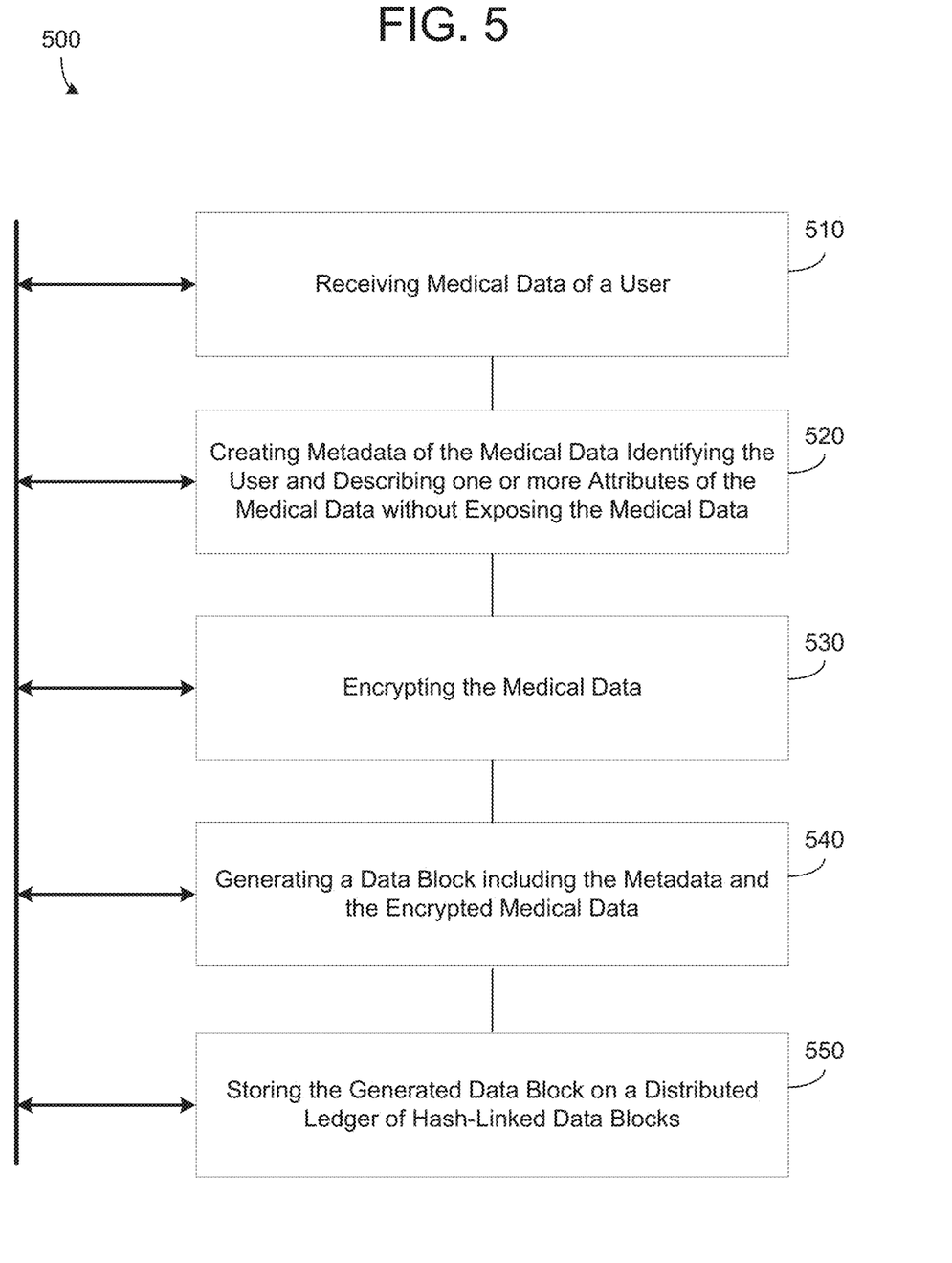
FIG. 5 is a diagram illustrating of method for generating and storing medical data via a blockchain according to example embodiments.

FIG. 5 illustrates a method 500 for generating and storing medical data via a blockchain according to example embodiments. For example, the method 500 may be performed by a blockchain node that is included within a network of nodes which implement the health-related blockchain described herein. Referring to FIG. 5, in 510, the method may include receiving medical data of a user. For example, the medical data may include health-related information such as medical records, medication information, vital signs, disease information, allergies, injuries, treatment information, doctor notes, and the like. The medical information may be information that is subject to regulation via HIPPA which prevents unauthorized exposure of such information.

In 520, the method may include creating metadata of the medical data. The metadata may include a unique identifier of the user, referred to herein as a public user ID, and a searchable description of the medical data which describes one or more attributes included in the medical data but does not expose the medical data. For example, the searchable description may provide a glance at the underlying medical information without divulging the medical information. In some embodiments, the searchable description of the medical data may include a textual description of a type of the medical data. For example, the metadata may recite, "health records," "vital signs," "treatment recommendations," "doctor's notes," "medication information," and the like. As another example, the metadata may also provide a list of information that is not protected by HIPPA such as a date/time, a doctor name, nurse name, hospital information, contact information, etc., and the like.

In 530, the method may include encrypting the medical data to generate encrypted medical data. For example, the encrypting of the medical data may include encrypting the medical data based on a symmetric key. The symmetric key may be generated by the blockchain node and may be a private key that is not available to other nodes/consumers. In 540, the method may include generating a data block having stored therein the created metadata of the medical data and the encrypted medical data. In some embodiments, the method may further include encrypting the symmetric key based on a public key and storing the encrypted symmetric key within the generated data block. Here, the public key may be known by the blockchain nodes of the system. Therefore, when a user consents to the revealing of their health/medical information, they may authorize the blockchain node to decrypt the symmetric key and share the symmetric key with a requesting consumer. In some cases, the blockchain node may encrypt the decrypted symmetric key using a public key of the data consumer to keep the symmetric key protected. In response to receiving the encrypted symmetric key, the consumer can decrypt the symmetric key based on their private key and use the symmetric key to decrypt the health information.

In 550, the method may include storing the generated data block within a distributed ledger such that the generated data block is hash-linked to a previous data block on the distributed ledger. For example, a portion of the previous data block (e.g., hashed medical information, metadata, user ID, etc.) may be encrypted and stored within a header or other section of the generated data block thereby linking the generated data block to a previous block in the distributed ledger.

In some embodiments, the method may further include outputting a search interface configured to receive input from a data consumer and perform a search of metadata stored on the distributed ledger based on the received input. Accordingly, a data consumer may identify health/medical information of interest without the system revealing the actual metadata. Instead, the system only provides the metadata which is not protected by HIPPA. Meanwhile, the encrypted medical data stored on the distributed ledger may satisfy security and privacy regulations of the medical data. In some embodiments, the method may further include receiving a request, via the distributed ledger, for access to the medical data from a data consumer via the search bar. In response, the method may include receiving consent from the data owner and storing consent for the data consumer to access the medical data via the distributed ledger. For example, the consent may provide access to the symmetric key used to encrypt the medical data encrypted based on a public key of the data consumer.

Figure 6A:
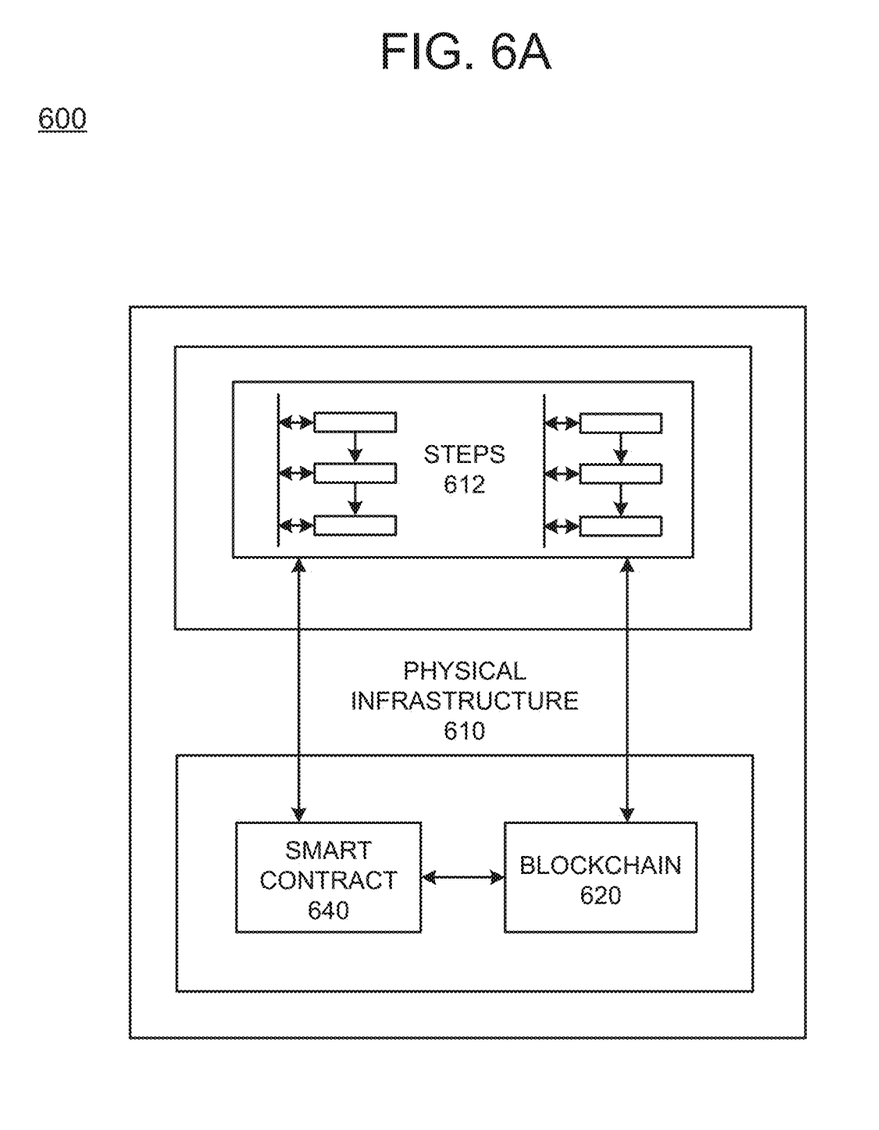
FIG. 6A is a diagram illustrating a physical infrastructure configured to perform various operations on the blockchain in accordance with one or more operations described herein, according to example embodiments.

FIG. 6A illustrates an example physical infrastructure configured to perform various operations on the blockchain in accordance with one or more of the example methods of operation according to example embodiments. Referring to FIG. 6A, the example configuration 600A includes a physical infrastructure 610 with a blockchain 620 and a smart contract 640, which may execute any of the operational steps 612 included in any of the example embodiments. The steps/operations 612 may include one or more of the steps described or depicted in one or more flow diagrams and/or logic diagrams. The steps may represent output or written information that is written or read from one or more smart contracts 640 and/or blockchains 620 that reside on the physical infrastructure 610 of a computer system configuration. The data can be output from an executed smart contract 640 and/or blockchain 620. The physical infrastructure 610 may include one or more computers, servers, processors, memories, and/or wireless communication devices.

Figure 6B:
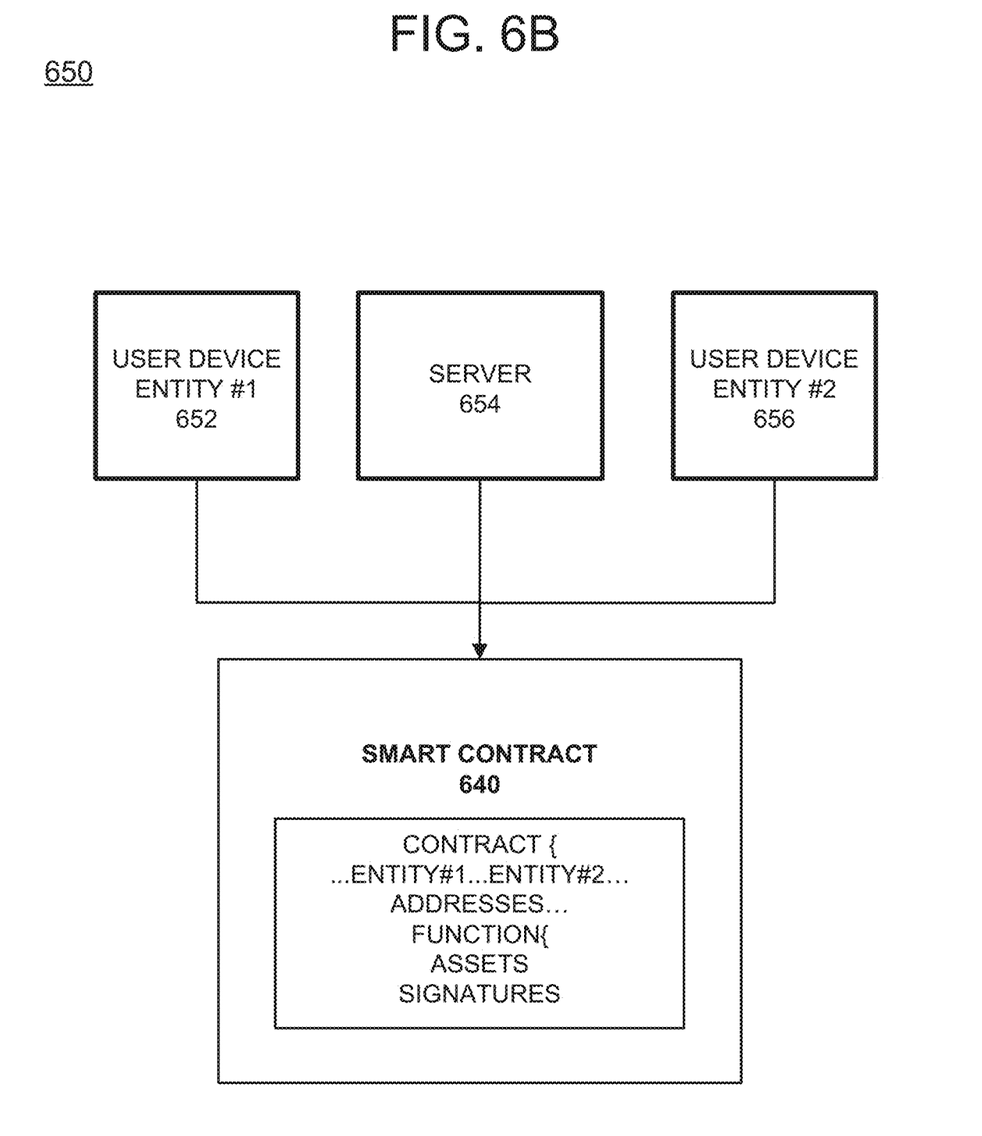
FIG. 6B is a diagram illustrating a smart contract configuration among contracting parties and a mediating server configured to enforce smart contract terms on a blockchain, according to example embodiments.

FIG. 6B illustrates an example smart contract configuration among contracting parties and a mediating server configured to enforce the smart contract terms on the blockchain according to example embodiments. Referring to FIG. 6B, the configuration 650B may represent a communication session, an asset transfer session or a process or procedure that is driven by a smart contract 640 which explicitly identifies one or more user devices 652 and/or 656. The execution, operations and results of the smart contract execution may be managed by a server 654. Content of the smart contract 640 may require digital signatures by one or more of the entities 652 and 656 which are parties to the smart contract transaction. The results of the smart contract execution may be written to a blockchain as a blockchain transaction.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 7 illustrates an example computer system architecture 700, which may represent or be integrated in any of the above-described components, etc.

Figure 7:
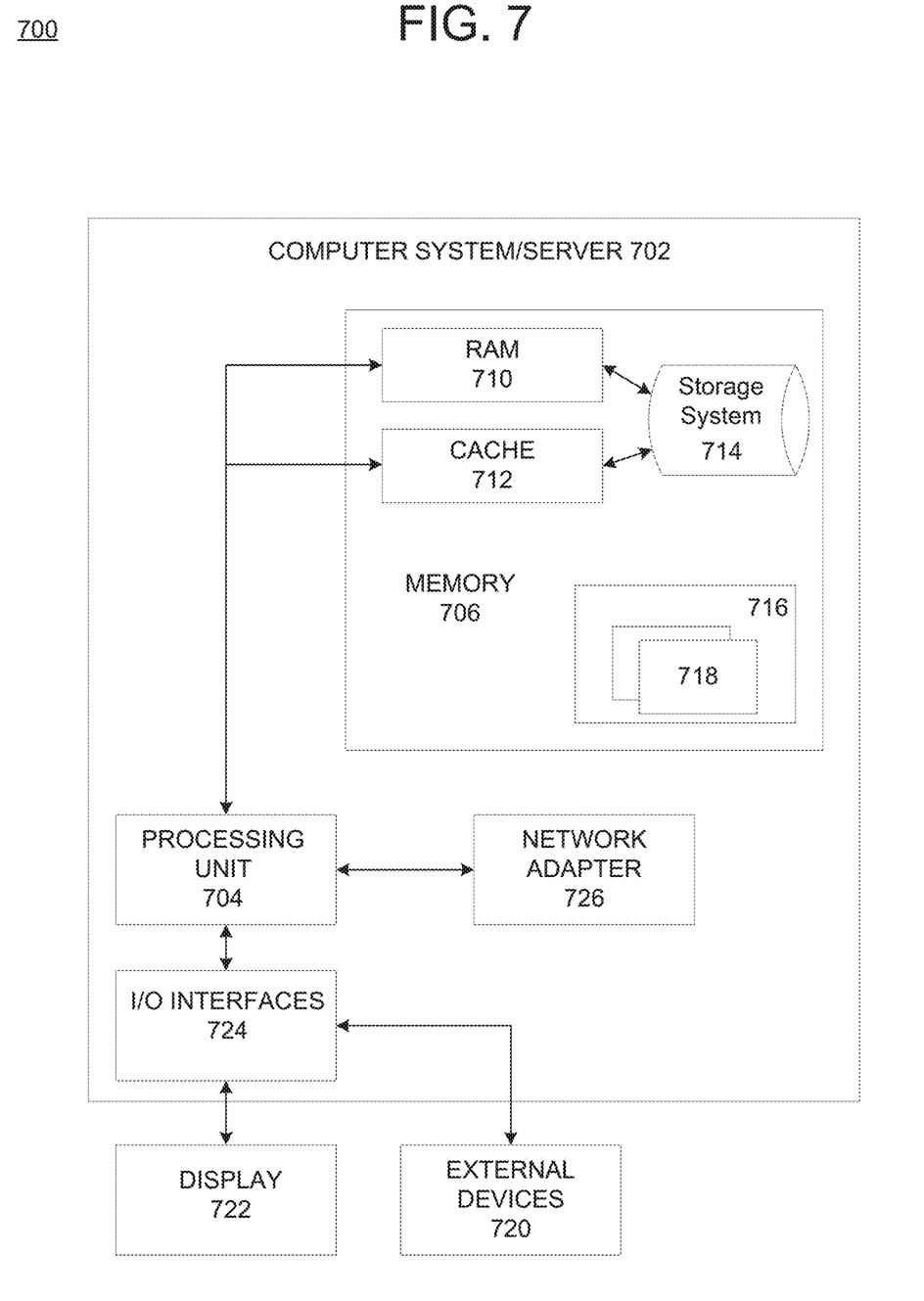
FIG. 7 is a diagram illustrating a computer system configured to support one or more of the example embodiments.

FIG. 7 is not intended to suggest any limitation as to the scope of use or functionality of embodiments of the application described herein. Regardless, the computing node 700 is capable of being implemented and/or performing any of the functionality set forth hereinabove.

In computing node 700 there is a computer system/server 702, which is operational with numerous other general purpose or special purpose computing system environments or configurations. Examples of well-known computing systems, environments, and/or configurations that may be suitable for use with computer system/server 702 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 702 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 702 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 702 in cloud computing node 700 is shown in the form of a general-purpose computing device. The components of computer system/server 702 may include, but are not limited to, one or more processors or processing units 704, a system memory 706, and a bus that couples various system components including system memory 706 to processor 704.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 702 typically includes a variety of computer system readable media. Such media may be any available media that is accessible by computer system/server 702, and it includes both volatile and non-volatile media, removable and non-removable media. System memory 706, in one embodiment, implements the flow diagrams of the other figures. The system memory 706 can include computer system readable media in the form of volatile memory, such as random-access memory (RAM) 710 and/or cache memory 712. Computer system/server 702 may further include other removable/non-removable, volatile/non-volatile computer system storage media. By way of example only, storage system 714 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 706 may include at least one program product having a set (e.g., at least one) of program modules that are configured to carry out the functions of various embodiments of the application.

Program/utility 716, having a set (at least one) of program modules 718, may be stored in memory 706 by way of example, and not limitation, as well as an operating system, one or more application programs, other program modules, and program data. Each of the operating system, one or more application programs, other program modules, and program data or some combination thereof, may include an implementation of a networking environment. Program modules 718 generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Computer system/server 702 may also communicate with one or more external devices 720 such as a keyboard, a pointing device, a display 722, etc.; one or more devices that enable a user to interact with computer system/server 702; and/or any devices (e.g., network card, modem, etc.) that enable computer system/server 702 to communicate with one or more other computing devices. Such communication can occur via I/O interfaces 724. Still yet, computer system/server 702 can communicate with one or more networks such as a local area network (LAN), a general wide area network (WAN), and/or a public network (e.g., the Internet) via network adapter 726. As depicted, network adapter 726 communicates with the other components of computer system/server 702 via a bus. It should be understood that although not shown, other hardware and/or software components could be used in conjunction with computer system/server 702. Examples, include, but are not limited to: microcode, device drivers, redundant processing units, external disk drive arrays, RAID systems, tape drives, and data archival storage systems, etc.

According to various embodiments, the network interface 726 may receive medical data of a user. In response, the processor 704 may create metadata of the medical data which includes a unique identifier of the user and a searchable description of the medical data which describes one or more attributes included in the medical data but does not expose the medical data. The processor 704 may encrypt the medical data to generate encrypted medical data. The encrypted medical data may satisfy one or more security and privacy regulations while the metadata may be made publicly available because it does not reveal sensitive information but may instead provide a generic description of the information. The processor 704 may generate a data block that has stored therein the created metadata of the medical data and the encrypted medical data, and store the generated data block within a distributed ledger such that the generated data block is hash-linked to a previous data block on the distributed ledger.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A computing system, comprising:
a processor configured to:
receive a medical file of a user comprising data that is subject to regulations by Health Insurance Portability and Accountability Act (HIPPA),
create metadata of the medical file which includes a unique identifier of the user and a searchable description of medical content included in the medical file, where the searchable description is created to include only descriptive terms that are not subject to regulations of HIPPA,
encrypt the medical data to generate encrypted medical data,
generate a data block that has stored therein the created metadata of the medical data which is not subject to the regulations of HIPPA and the encrypted medical data, and
store the generated data block within the blockchain.

2. The computing system of claim 1, wherein the searchable description of the medical content comprises a generic textual description of one or more of a type of treatment performed for the user, a medical condition of the user, and disease information of the user.

3. The computing system of claim 1, wherein the processor is configured to encrypt the medical data based on a symmetric key.

4. The computing system of claim 3, wherein the processor is further configured to encrypt the symmetric key based on a public key and store the encrypted symmetric key within the generated data block.

5. The computing system of claim 1, wherein the processor is further configured to generate and output a search interface configured to receive input and perform a search of metadata stored on the distributed ledger based on the received input.

6. The computing system of claim 1, wherein the encrypted medical data stored on the distributed ledger satisfies security and privacy regulations of the medical data.

7. The computing system of claim 1, wherein the processor is further configured to receive a request, via the distributed ledger, for access to the medical data from a data consumer.

8. The computing system of claim 1, wherein the processor is further configured to store, on the blockchain, consent from the user for accessing the medical data which includes an encryption key used to encrypt the medical data.

9. A method, comprising:
receiving a medical file of a user comprising data that is subject to regulations by Health Insurance Portability and Accountability Act (HIPPA);
creating metadata of the medical file which includes a unique identifier of the user and a searchable description of medical content included in the medical file, where the searchable description is created to include only descriptive terms that are not subject to regulations of HIPPA;
encrypting the medical data to generate encrypted medical data;
generating a data block having stored therein the created metadata of the medical data which is not subject to the regulations of HIPPA and the encrypted medical data; and
storing the generated data block within the blockchain.

10. The method of claim 9, wherein the searchable description of the medical content comprises a generic textual description of one or more of a type of treatment performed for the user, a medical condition of the user, and disease information of the user.

11. The method of claim 9, wherein the encrypting the medical data comprises encrypting the medical data based on a symmetric key.

12. The method of claim 11, further comprising encrypting the symmetric key based on a public key and storing the encrypted symmetric key within the generated data block.

13. The method of claim 9, further comprising outputting a search interface configured to receive input and perform a search of metadata stored on the distributed ledger based on the received input.

14. The method of claim 9, wherein the encrypted medical data stored on the distributed ledger satisfies security and privacy regulations of the medical data.

15. The method of claim 9, further comprising receiving a request, via the distributed ledger, for access to the medical data from a data consumer.

16. The method of claim 9, wherein the method further comprises storing, on the blockchain, consent from the user for accessing the medical data which includes an encryption key used to encrypt the medical data.

17. A non-transitory computer readable medium comprising instructions, that when read by a processor, cause the processor to perform:
receiving a medical file of a user comprising data that is subject to regulations by Health Insurance Portability and Accountability Act (HIPPA);
creating metadata of the medical file which includes a unique identifier of the user and a searchable description of medical content included in the medical file, where the search description is created to include only descriptive terms that are not subject to regulations of HIPPA;
encrypting the medical data to generate encrypted medical data;
generating a data block having stored therein the created metadata of the medical data which is not subject to the regulations of HIPPA and the encrypted medical data; and
storing the generated data block within the blockchain.

18. The non-transitory computer readable medium of claim 17, wherein the searchable description of the medical content comprises a generic textual description of one or more of a type of treatment performed to the user, a medical condition of the user, and disease information of the user.

19. The non-transitory computer readable medium of claim 17, wherein the method further comprises outputting a search interface configured to receive input and perform a search of metadata stored on the distributed ledger based on the received input.

20. The non-transitory computer readable medium of claim 17, wherein the created metadata and the encrypted medical data stored on the distributed ledger satisfy security and privacy regulations of the medical data.

* * * * *